(12) United States Patent
Iwakiri

(10) Patent No.: US 7,928,402 B2
(45) Date of Patent: Apr. 19, 2011

(54) RADIATION IMAGE DETECTOR

(75) Inventor: Naoto Iwakiri, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 444 days.

(21) Appl. No.: 12/180,995

(22) Filed: Jul. 28, 2008

(65) Prior Publication Data

US 2009/0084993 A1 Apr. 2, 2009

(30) Foreign Application Priority Data

Jul. 27, 2007 (JP) .................................. 2007-195900

(51) Int. Cl.
*G01T 1/24* (2006.01)
*H01L 27/146* (2006.01)
*G01N 23/04* (2006.01)
(52) U.S. Cl. ................ 250/370.15; 250/370.09; 250/591
(58) Field of Classification Search ............. 250/370.15, 250/370.09, 591
See application file for complete search history.

(56) References Cited

U.S. PATENT DOCUMENTS

| 4,873,439 | A | * | 10/1989 | Hagelstein et al. .......... 250/591 |
| 6,121,620 | A | | 9/2000 | Tashiro et al. |
| 6,359,281 | B1 | * | 3/2002 | Pawlak et al. ............ 250/370.09 |
| 7,034,333 | B1 | * | 4/2006 | Fink ................................ 257/48 |

FOREIGN PATENT DOCUMENTS

JP 08-106869 A 4/1996

* cited by examiner

*Primary Examiner* — David P Porta
*Assistant Examiner* — Mindy Vu
(74) *Attorney, Agent, or Firm* — Sughrue Mion, PLLC

(57) ABSTRACT

A radiation image detector includes a radiation-image-detector main body and a vacuum container. The radiation-image-detector main body generates charges by irradiation with an electromagnetic wave for recording that carries a radiation image and records the radiation image by accumulating the charges. The vacuum container is sealed to store the radiation-image-detector main body in a vacuum.

7 Claims, 1 Drawing Sheet

RADIATION IMAGE DETECTOR

BACKGROUND OF THE INVENTION

1. Field of the Invention

The present invention relates to a radiation image detector that generates charges (electric charges) by irradiation with an electromagnetic wave for recording, the electromagnetic wave carrying a radiation image, and that records the radiation image by accumulating the charges.

2. Description of the Related Art

These days, in the field of radiography using X-rays (radiation) for medical diagnosis or the like, various kinds of X-ray radiography apparatuses have been proposed and used practically. The X-ray radiography apparatuses use radiation image detectors that include semiconductors as the main parts thereof and detect X-rays that have passed through subjects. Accordingly, image signals representing X-ray images related to the subjects are obtained.

Further, as the radiation image detectors that are used in the X-ray radiography apparatuses, various kinds of radiation image detectors have been proposed. For example, if the radiation image detectors are classified based on the charge generation process for converting X-rays into charges, there are a radiation image detector using an indirect conversion method, a radiation image detector using a direct conversion method and the like. The radiation image detector using the indirect conversion method obtains signal charges by detecting, at a photoconductive layer, fluorescence output from a phosphor by irradiation with X-rays, temporarily accumulates the signal charges in a charge accumulation portion, converts the accumulated charges into image signals and outputs the image signals. The radiation image detector using the direct conversion method temporarily accumulates signal charges that have been generated in a photoconductive layer by irradiation with X-rays in a charge accumulation portion, converts the accumulated charges into image signals and outputs the image signals.

Meanwhile, if the radiation image detectors are classified based on the charge readout process for reading out the accumulated charges from the outside thereof, there are a radiation image detector using an optical readout method, a radiation image detector using an electrical readout method, as disclosed in Japanese Unexamined Patent Publication No. 8 (1996)-106869, and the like. In the optical readout method, charges are read out from the radiation image detector by irradiating the radiation image detector with readout light (an electromagnetic wave for readout). In the electrical readout method, charges are read out from the radiation image detector by scan-driving a switching device, such as a TFT (thin film transistor), a CCD (charge coupled device) or a CMOS (complementary metal oxide semiconductor) sensor, connected to the charge accumulation portion.

Further, the applicant of the priority application of the present application proposed a solid-state detector using an improved direct conversion method in U.S. Pat. No. 6,121, 620 and the like. The solid-state detector using the improved direct conversion method uses the direct conversion method and the optical readout method. In the solid-state detector using the improved direct conversion method, a photoconductive layer for recording, a charge transfer layer and a photoconductive layer for readout are deposited one on another in this order. The photoconductive layer for recording exhibits photoconductivity by irradiation with recording light (X-rays, fluorescence generated by irradiation with X-rays or the like). The charge transfer layer substantially acts as an insulator with respect to charges that have the same polarity with the polarity of latent image charges. Further, the charge transfer layer substantially acts as a conductor with respect to transfer charges that have a polarity opposite to the polarity of the latent image charges. The photoconductive layer for readout exhibits photoconductivity by irradiation with an electromagnetic wave for readout. In the solid-state detector using the improved direct conversion method, signal charges (latent image charges) that carry image information are accumulated at the interface (charge accumulation portion) between the photoconductive layer for recording and the charge transfer layer.

Here, the photoconductive layer of the radiation image detector as described above is made of a-Se or the like, for example. When the temperature exceeds a glass transition temperature, a-Se or the like is crystallized. Further, when humidity is high, condensation of vapor occurs, thereby crystallizing a-Se.

SUMMARY OF THE INVENTION

In view of the foregoing circumstances, it is an object of the present invention to provide a radiation image detector that is not influenced by a change in temperature or humidity.

A radiation image detector according to the present invention is a radiation image detector comprising:

a radiation-image-detector main body that generates charges by irradiation with an electromagnetic wave for recording, the electromagnetic wave carrying a radiation image, and that records the radiation image by accumulating the charges; and a vacuum container that is sealed to store the radiation-image-detector main body in a vacuum.

Further, in the radiation image detector according to the present invention, a support unit for supporting the radiation-image-detector main body, the support unit being made of a heat insulator, may be provided on one side of the radiation-image-detector main body that is opposite to an irradiation side thereof, the irradiation side being irradiated with the electromagnetic wave for recording.

Further, a part of the outer surface or the entire outer surface of the vacuum container may be made of a material that reflects infrared rays.

Further, a readout circuit for reading out an image signal from the radiation-image-detector main body or a drive circuit for driving the radiation-image-detector main body may be provided on the outside of the vacuum container.

Further, the vacuum container may be made of a material that functions as an electric shield (a shield against an electric field or the like).

Further, the vacuum container may be made of a material that functions as a magnetic shield (a shield against a magnetic field or the like).

Further, the degree of vacuum in the vacuum container may be greater than or equal to 102 Pa and less than or equal to $5\times10^4$ Pa.

In the radiation image detector according to the present invention, the radiation-image-detector main body is stored in a vacuum by sealing the container. Therefore, a heat insulation effect can be achieved by the structure. Hence, it is possible to prevent the temperature of the radiation-image-detector main body from exceeding the glass transition temperature of a-Se by an influence of the temperature on the outside of the radiation image detector. Further, it is possible to prevent crystallization of a-Se.

Further, since no air (outer air) is present around the radiation-image-detector main body because of the vacuum structure, it is possible to prevent condensation of vapor. Therefore, for example, when the radiation-image-detector main body uses an indirect conversion method and CsI:Tl as a wavelength conversion material, it is possible to prevent CsI:Tl from deliquescing. Further, it is possible to prevent crystallization of a-Se. Further, it is possible to prevent breakage of insulation caused by condensation of vapor during application of high voltage.

Further, the sound insulation effect achieved by the vacuum structure can prevent resonance of the radiation-image-detector main body caused by external disturbance noise. Further, it is possible to prevent unevenness (irregularity) in the radiation image that is read out from the radiation-image-detector main body.

Further, in the radiation image detector according to the present embodiment, if a support unit for supporting the radiation-image-detector main body, the support unit being made of a heat insulator, is provided on one side of the radiation-image-detector main body that is opposite to an irradiation side thereof, the irradiation side being irradiated with the electromagnetic wave for recording, it is possible to further reduce the influence of the outside temperature.

Further, if a part of the outer surface or the entire outer surface of the vacuum container is made of a material that reflects infrared rays, it is possible to prevent an increase in temperature caused by irradiation with infrared rays.

Further, if a readout circuit for reading out an image signal from the radiation-image-detector main body or a drive circuit for driving the radiation-image-detector main body is provided on the outside of the vacuum container, it is possible to prevent an increase in the temperature of the radiation-image-detector main body by heat output from the radiation circuit and the drive circuit.

DESCRIPTION OF THE PREFERRED EMBODIMENTS

Figure 1:
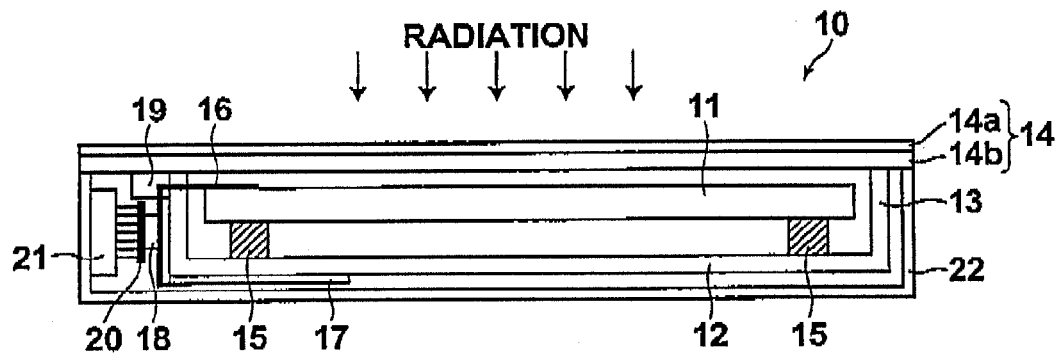
FIG. 1 is a cross-sectional diagram illustrating an embodiment of a radiation image detector according to the present invention.

Hereinafter, an embodiment of the present invention will be described in detail with reference to the attached drawings. FIG. 1 is a cross-sectional diagram illustrating the schematic structure of a radiation image detector according to an embodiment of the present invention.

A radiation image detector 10 includes a radiation-image-detector main body 11 and a vacuum container 12. The radiation-image-detector main body 11 generates charges by irradiation with a radiation and records a radiation image by accumulating the charges. The vacuum container 12 is sealed to store the radiation-image-detector main body 11 in a vacuum.

The radiation-image-detector main body 11 may be any kind of radiation-image detector main body as long as the radiation-image-detector main body 11 can generate charges by irradiation with a radiation and record a radiation image by accumulating the charges. The radiation-image-detector main body 11 may use a direct conversion method. Alternatively, the radiation-image-detector main body 11 may use an indirect conversion method and include a wavelength conversion material, such as CsI:Tl. Further, the radiation-image-detector main body 11 may use an electrical readout method. Alternatively, the radiation-image-detector main body 11 may use an optical readout method. In the present embodiment, the radiation-image-detector main body 11 uses a direct conversion method and an electrical readout method. Further, in the present embodiment, the radiation-image-detector main body 11 includes a photoconductive layer made of a-Se.

The vacuum container 12 includes an accommodation portion 13 and a top plate portion 14. The radiation-image-detector main body 11 is housed in the accommodation portion 13 and the top plate portion 14 is a lid for the accommodation portion 13. Space enclosed by the accommodation portion 13 and the top plate portion 14 that have been sealed is a vacuum. It is desirable that the degree of vacuum in the space is greater than or equal to $10^2$ Pa and less than or equal to $5 \times 10^4$ Pa.

Further, it is desirable that the accommodation portion 13 is made of a material that functions as an electric shield (a shield against an electric field). For example, it is desirable that the accommodation portion 13 is made of metal. Alternatively, the accommodation portion 13 may be made of a material that is produced by coating resin with metal. Alternatively, the accommodation portion 13 may be made of a material that functions as a magnetic shield (a shield against a magnetic field). For example, the accommodation portion 13 may be made of a material, such as a permalloy, which has high magnetic permeability, and a material called as Permalloy C according to the JIS (Japanese Industrial Standard). Permalloy C is obtained by adding Mo, Cu, Cr or the like to a permalloy.

The top plate portion 14 is composed of an aluminum vapor-deposition coating 14a and a carbon plate 14b. The aluminum vapor-deposition coating 14a reflects infrared rays and the carbon plate 14b absorbs infrared rays. Further, the aluminum vapor-deposition coating 14a and the carbon plate 14b are attached in such a manner that the aluminum vapor-deposition coating 14a is positioned on the outer side of the accommodation portion 13. Further, it is desirable that parylene coating is applied to the carbon plate 14b so that the vacuum in the vacuum container 12 can be maintained.

The radiation-image-detector main body 11 is supported by heat-insulation support units 15, which are made of heat insulation material (heat insulator). The heat-insulation support units 15 are provided on one side of the radiation-image-detector main body 11 that is opposite to an irradiation side thereof, the irradiation side being irradiated with a radiation.

Further, a TCP (Tape Carrier Package) 16 is connected to the radiation-image-detector main body 11. The TCP 16 is drawn out to the outside of the vacuum container 12 and bent along the outer surface of the vacuum container 12. Further, an end of the TCP 16 is connected to a printed circuit board 17 (a printed substrate, a printed board or the like) in which a predetermined image processing circuit has been provided. The printed circuit board 17 is provided on one side of the radiation-image-detector main body 11 that is opposite to an irradiation side thereof, the irradiation side being irradiated with a radiation. Further, a seal material 19 is provided at a hole portion that has been formed on the vacuum container 12 to draw out the TCP 16 to the outside of the vacuum container 12. The seal material 19 is provided to maintain the degree of vacuum in the vacuum container 12.

Further, an IC chip 18 including a readout circuit (amplifier) and a drive circuit (gate driver) is provided in the TCP 16. The readout circuit reads out image signals from the radiation-image-detector main body 11 and the drive circuit drives the TFT. The IC chip 18 is provided on the outside of the vacuum container 12.

Further, a heat pipe and a heat radiator 20 are provided for the IC chip 18 to make heat that has been generated in the IC chip 18 escape (be output) therefrom. Further, a fan 21 is provided to make the heat in the heat radiator 20 escape therefrom. Further, a Peltier device may be provided to cool the IC chip 18.

Further, a case 22 is provided in such a manner to surround the entire outer surface of the radiation image detector 10.

Further, in the radiation image detector 10 according the aforementioned embodiment, it is desirable that a convex curl is formed on the top plate portion 14 in advance so that when the inside of the vacuum container 12 is vacuumized, the top plate portion 14 does not concavely bend toward the inside of the vacuum container 12.

Figure 2A:
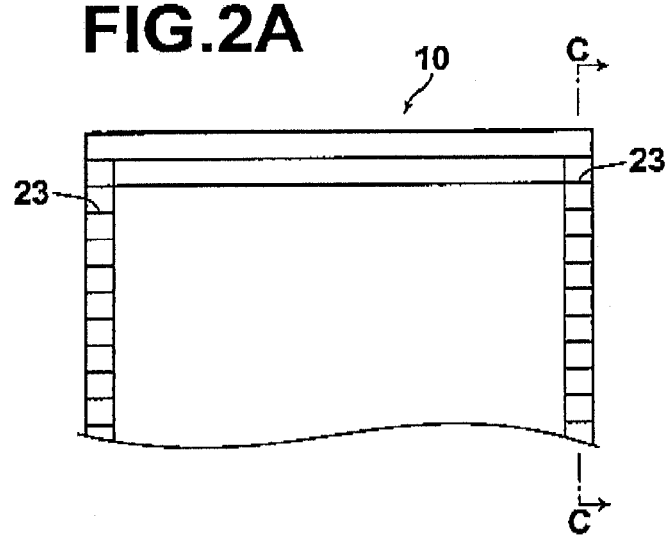
FIG. 2A is a top view of another embodiment of the radiation image detector according to the present invention.
Figures 2B, 2C:
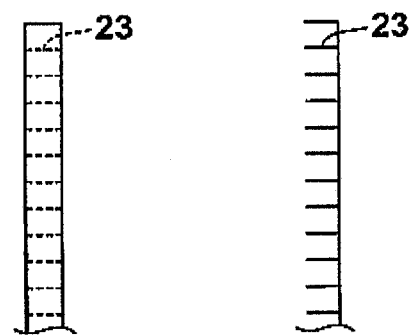
FIG. 2B is a side view of the embodiment of the radiation image detector according to the present invention.
FIG. 2C is a sectional diagram at line C-C in FIG. 2A.

Further, as illustrated in FIGS. 2A through 2C, ribs 23 may be provided to prevent the top plate portion 14 from being bent toward the inside of the vacuum container 12. FIG. 2A is a top view of the radiation image detector 10 and FIG. 2B is a side view of the radiation image detector 10. Further, FIG. 2C is a sectional diagram at line C-C in FIG. 2A. It is desirable that the ribs 23 are not formed in an image area in which the radiation image is recorded. When the ribs 23 are formed in the image area, it is desirable that the thickness of the ribs 23 is sufficiently thin so that the ribs 23 are not captured in a radiation image, in other words, so that the ribs 23 do not appear in the radiation image.

What is claimed is:

1. A radiation image detector comprising:
   a radiation-image-detector main body that generates charges by irradiation with an electromagnetic wave for recording, the electromagnetic wave carrying a radiation image, and that records the radiation image by accumulating the charges; and
   a vacuum container that is sealed to store the radiation-image-detector main body in a vacuum.

2. A radiation image detector, as defined in claim 1, wherein a support unit for supporting the radiation-image-detector main body, the support unit being made of a heat insulator, is provided on one side of the radiation-image-detector main body that is opposite to an irradiation side thereof, the irradiation side being irradiated with the electromagnetic wave for recording.

3. A radiation image detector, as defined in claim 1, wherein a part of the outer surface or the entire outer surface of the vacuum container is made of a material that reflects infrared rays.

4. A radiation image detector, as defined in claim 1, wherein a readout circuit for reading out an image signal from the radiation-image-detector main body or a drive circuit for driving the radiation-image-detector main body is provided on the outside of the vacuum container.

5. A radiation image detector, as defined in claim 1, wherein the vacuum container is made of a material that functions as an electric shield.

6. A radiation image detector, as defined in claim 1, wherein the vacuum container is made of a material that functions as a magnetic shield.

7. A radiation image detector, as defined in claim 1, wherein the degree of vacuum in the vacuum container is greater than or equal to $10^2$ Pa and less than or equal to $5 \times 10^4$ Pa.

* * * * *